United States Patent [19]

Fujita et al.

[11] Patent Number: 5,079,350
[45] Date of Patent: Jan. 7, 1992

[54] PROCESS FOR THE PRODUCTION OF ALKYL GLYCOSIDE OR AQUEOUS SOLUTION THEREOF

[75] Inventors: Tadaaki Fujita; Kiyoshi Aimono; Kunizo Hashiba; Koichi Ohori, all of Wakayama, Japan

[73] Assignee: Kao Corporation, Tokyo, Japan

[21] Appl. No.: 501,218

[22] Filed: Mar. 29, 1990

[30] Foreign Application Priority Data

Sep. 19, 1989 [JP] Japan ................... 1-242529

[51] Int. Cl.$^5$ .......................... C07G 3/00; C07H 1/00; C07H 3/00
[52] U.S. Cl. ................... 536/18.6; 536/18.5; 536/124; 536/4.1
[58] Field of Search ............. 536/18.6, 18.5, 124, 536/4.1

[56] References Cited

U.S. PATENT DOCUMENTS

| | | | |
|---|---|---|---|
| 3,565,885 | 2/1971 | Molotsky et al. | 536/18.6 |
| 3,598,865 | 8/1971 | Lew | 536/18.6 |
| 3,839,318 | 10/1974 | Mansfield | 536/18.6 |
| 4,223,129 | 9/1980 | Roth et al. | 536/18.6 |
| 4,557,729 | 12/1985 | McDaniel et al. | 536/18.5 |
| 4,713,447 | 12/1987 | Letton | 536/18.6 |

OTHER PUBLICATIONS

Derwent Abstract of Japanese Patent Application No. 58-189195.
Derwent Abstract of Japanese Patent Application No. 59-139397.
Derwent Abstract of Japanese Patent Application No. 62-192396.
Derwent Abstract of Japanese Patent Application No. 1-47796.

*Primary Examiner*—Ronald W. Griffin
*Assistant Examiner*—Everett White
*Attorney, Agent, or Firm*—Sughrue, Mion, Zinn, Macpeak & Seas

[57] ABSTRACT

A process for the production of an alkyl glycoside or an aqueous solution thereof is disclosed, comprising the steps of (1) reacting a sugar with alcohol to obtain an alkyl glycoside reaction product containing unreacted alcohol, (2) establishing a moving liquid film of the alkyl glycoside reaction product and (3) contacting the moving liquid film with steam or an inert gas at a temperature of from 50° to 200° C. The alkyl glycoside or aqueous solution thus obtained contains little unreacted alcohol and is excellent in hue and odor.

10 Claims, No Drawings

PROCESS FOR THE PRODUCTION OF ALKYL GLYCOSIDE OR AQUEOUS SOLUTION THEREOF

FIELD OF THE INVENTION

This invention relates to a proces for the production of an alkyl glycoside or aqueous solution thereof containing a small amount of an unreacted higher alcohol (hereinafter "unreacted alcohol") excellent in hue and odor.

BACKGROUND OF THE INVENTION

An alkyl glycoside is a sugar derivative surfactant which is less irritating than other surfactants. Also, though it is a noninonic surfactant, alkyl glycoside form a stable foam per se, and furthermore, exert a foam-stabilizing effect on other anionic surfactants. These characteristics have make alkyl glycosides highly noteworthy.

Although alkyl glycosides as novel surfactants the above described noteworthy characteristics, it is quite difficult to produce them in the form of a commercially useful product.

An alkyl glycoside is usually prepared by reacting a sugar with a higher alcohol. In practice, the unreacted alcohol must be removed from the alkyl glycoside product before being used as a surfactant. It is preferable to remove as much unreacted alcohol as possible from the alkyl glycoside reaction product, because the remaining alcohol imparts an undesirable odor to the product.

The excessive alcohol can be separated and removed by a conventional method such as distillation. However alkyl glycosides generally have high melting points, which makes it necessary to heat the alkyl glycoside to a fluid state in order to transport the same by means of a pump.

On the other hand, most alkyl glycosides have a limited heat stability. Thus, the hue of the alkyl glycoside product tends to deteriorate and sugar alcohols are formed even by slightly heating.

Therefore, various methods have been proposed to remove the unreacted alcohol from the alkyl glycoside reaction product without deteriorating the hue. For example, JP-A-58-194902 (the term "JP-A" as used herein means an "unexamined published Japanese patent application") (corresponding to U.S. Pat. No. 3,565,885) discloses a process wherein a film of a reaction product containing excess unreacted alcohol is formed, and the excess alcohol is evaporated at a relatively high temperature and within an extremely short residence time. JP-A-64-47796 discloses a process wherein a small amount of a short-chain alkyl sugar having 1 to 5 carbon atoms is used, and the flowability of the product is improved at a lower temperature to thereby evaporate the excess alcohol. JP-A-62-192396 discloses a process wherein one or more viscosity depressants is added having a boiling point at 760 mb higher than that of the unreacted alcohol by at least 50° C. and having detergent, emulsifier or detergent-aid properties. The excess alcohol is then removed at a temperature lower than the decomposition temperature of the alkyl glycoside by at least 20° C. However each of these known processes is disadvantageous in that the thus obtained alkyl glycoside has an unsatisfactory hue, the remaining unreacted alcohol can only be removed to the extent of 0.5 % by weight based on the alkyl glycoside without deteriorating the hue of the alkyl glycoside, or a secondary component other than the alkyl glycoside is required.

Furthermore, JP-A-61-33193 (corresponding to U.S. Pat. No. 4,557,729) describes a process for improving the hue of an alkyl glycoside which comprises bleaching the product with the use of hydrogen peroxide and sulfur dioxide. In this case, however, the remaining alcohol is oxidized into an aldehyde which rapidly deteriorates the odor of the product, and the resulting product has poor storage stability. This process is also unsatisfactory for the improvement of the hue of an alkyl glycoside.

SUMMARY OF THE INVENTION

The present inventors have conducted extensive investigations in order to establish a process for economically and advantageously producing an alkyl glycoside, containing a small amount of unreacted alcohol, and excellent in hue and odor, by a simple procedure without the need for employing an additional reaction component, to thereby achieve the present invention.

Accordingly, the present invention provides a process for the production of an alkyl glycoside or aqueous solution thereof excellent in hue and odor, and containing little unreacted alcohol, comprising the steps of (1) reacting a sugar with alcohol to obtain an alkyl glycoside reaction product containing unreacted alcohol, (2) establishing a moving liquid film of the alkyl glycoside reaction product, and (3) contacting the moving liquid film with steam or an inert gas at a temperature of 50° to 200° C. to remove the unreacted higher alcohol.

DETAILED DESCRIPTION OF THE INVENTION

The alkyl glycoside reaction product of the present invention is obtained by a commonly known method. For example, the alkyl glycoside reaction product may be obtained either by directly reacting a sugar with a higher alcohol in the presence of an acid catalyst, or by preliminarily reacting a sugar with a lower alcohol (for example, methanol, ethanol, propanol, butanol) to thereby obtain a lower alkyl glycoside which is then reacted with a higher alcohol.

The higher alcohol for in the process of the present invention is represented by formula (I):

$$R^1(OR^2)_xOH \tag{I}$$

wherein
$R^1$ represents a straight-chain or branched alkyl, alkenyl or alkylphenyl group having from 6 to 22 carbon atoms;
$R^2$ represents an alkylene group having 2 to 4 carbon atoms; and
x indicates a mean value and is a number equal to 0 to 5.

Specific examples of the higher alcohol represented by formula (I) include a straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and 2-octyldecanol; an alkenol such as hexenol, heptenol, octenol, nonenol, decenol, undecenol, dodecenol, tridecenol, tetradecenol, pentadecenol, hexadecenol, heptadecenol and octadecenol; and alkylphenols such as octylphenol and nonylphenol. These alcohols or alkylphenols may be used either alone or a mixture of two or more of them. Further, an alkylene oxide adduct of these alcohols or alkylphenols can be used for the production of alkyl glycoside.

The sugar for use as the starting material for the production of the alkyl glycoside according to the present invention is selected from monosaccharides, oligosaccharides, and polysaccharides. Examples of the monosaccharides include aldoses such as allose, altrose, glucose, mannose, gulose, idose, galactose, talose, ribose, arabinose, xylose, lyxose. Examples of the oligosaccharides include maltose, lactose, sucrose and maltotriose. Examples of the polysaccharides include hemicellulose, inulin, dextrin, dextran, xylan, starch and hydrolyzed starch As the alkyl glycoside to be used according to the process of the present invention, those represented by formula (II) are particularly preferable:

wherein $R_1$ is an alkyl, alkenyl, or alkylphenyl group having from 6 to 22 carbon atoms;

$R_2$ is an alkylene group having from 2 to 4 carbon atoms;

G is a residual group originating from a reducing sugar having 5 to 6 carbon atoms;

x indicates a mean value and is a number equal to 0 to 5; and y indicates a mean value and is a number equal to 1 to 10.

In the present invention, the production of an alkyl glycoside may be conducted with the use of the above described starting materials under known conditions (for example, catalyst, temperature) as disclosed, for example, in JP-B-47-24532 (the term "JP-B" as used herein means an "examined Japanese patent publication") (corresponding to U.S. Pat. No. 3,598,865), U.S. Pat. No. 3,839,318, European Patent 092355, JP-A-59-139397, and JP-A-58-189195.

As described above, the unreacted alcohol can be removed from an alkyl glycoside reaction product containing the unreacted alcohol by a known method such as distillation or solvent extraction. However, a preferable method for removing the unreacted alcohol comprises establishing a filmy flow of the alkyl glycoside reaction product containing the unreacted alcohol and then applying heat and vacuum thereto. In this case, the content of the unreacted alcohol can be lowered to an amount of 2 % by weight or less as described, for example, in JP-A-58-194902 (corresponding to U.S. Pat. No. 3,565,885).

In this method, however, it is necessary to treat the alkyl glycoside reaction product at a higher temperature in order to reduce the content of the unreacted alcohol to 0.5 % by weight or below, and preferably 0.2 % by weight or below, based on the alkyl glycoside. Thus, the resulting thermal decomposition of the alkyl glycoside deteriorates the qualities (for example, hue and odor) of the product. Accordingly this method is unsuitable for producing an alkyl glycoside having excellent hue and color qualities.

In order to avoid processing the alkyl glycoside product at such high temperatures, it has been proposed to elevate the degree of vacuum. However, the pressure must be reduced to 0.5 mmHg or less in order to remove such a large amount of the unreacted alcohol as described above. In order to achieve such a high degree of vacuum, specialized equipment is needed, which requires a considerably large investment. When a condenser at low temperature is employed, the alcohol is also evaporated outside of the system, such that expensive pollution control equipment is required.

However, the present inventors have discovered that the unreacted alcohol contained in an alkyl glycoside reaction product can be almost completely removed, without the use of high-vacuum equipment, by running said reaction product to establishing a moving liquid film of the alkyl glycoside reaction product, and then contacting the moving liquid film with steam or an inert gas. The unreacted alcohol is thereby efficiently removed under a relatively low degree of vacuum, to achieve the present invention.

An alkyl glycoside reaction product obtained by a known method, and from which catalysts have been removed by neutralization, may be used in the present invention. In this case, a multi-step operation is conducted. Alternately, an aqueous solution of the alkyl glycoside reaction product may be processed in accordance with the present invention. In this case, the concentration of the aqueous solution is not particularly restricted. It is preferable to preliminarily reduce the concentration of the unreacted alcohol in the alkyl glycoside reaction product to 3 to 10 % by weight by a known method (for example, distillation, solvent extraction), prior to processing in accordance with present invention.

The process of the present invention is carried out at a temperature of from 50° to 200° C., and preferably 120° to 170° C. At a temperature exceeding 200° C., the thermal decomposition of the alkyl glycoside deteriorates the hue and odor of the product. On the other hand, at a temperature lower than 50° C., the viscosity of the product is elevated to an undesirable level. The processing pressure is 300 mmHg or less, and preferably 150 mmHg or less. The amount of the steam or inert gas to be contacted with the moving liquid film is not particularly restricted, and may be appropriately selected depending on the desired degree of removal of the unreacted alcohol.

In the process of the present invention, a steam or inert gas stream reduces the partial pressure of the evaporated alcohol, thereby the evaporation under these stream promotes the further removal of unreacted alcohol from the alkyl glycoside.

The steam or inert gas stream may be effectively applied in either counter current, concurrent or cross current direction with respect to the moving liquid film. Any inert gas may be used as long as it does not react with the alkyl glycoside reaction product. Preferable examples thereof include nitrogen, carbon dioxide and air.

A thinner film of the moving liquid film is preferable, although the thickness of the film is not particularly limited. The film thickness obtained using a conventional thin film evaporator is satisfactory for use in the present invention. The film thickness is preferably about 10 mm or less.

A conventional thin film evaporator may be used to provide the moving liquid film. For example, a Smith thin film evaporator (manufactured by SHINKO PAN- TEC Co.), a kontro evaporator (manufactured by Hitachi Ltd.) and a LUWA thin film evaporator (manufactured by LUWA Co.) may be employed therefor. Although a film is forcedly formed in each of the above-described devices, a spontaneous film type evaporator such as a falling film evaporator may also be used.

To further illustrate the present invention, the following nonlimiting Examples are provided below. Unless otherwise indicated, all percentages are by weight.

EXAMPLE 1

(a) An alkyl glycoside reaction product was obtained by reacting, in a conventional manner, 5 molar equivalents, based on anhydrous glucose, of decyl alcohol and 0.014 molar equivalent, based on anhydrous glucose, of p-toluenesulfonic acid monohydrate with the anhydrous glucose. Next, the excess unreacted decyl alcohol was distilled at 150° C. and 5 mmHg to provide an alkyl glycoside reaction product containing 2.8 % by weight of the unreacted decyl alcohol.

(b) The alkyl glycoside reaction product thus prepared was introduced into a Smith thin film evaporator (manufactured by SHINKO PANTEC Co.; heat transfer area: 0.2 m$^2$) to provide a moving liquid film thereof while blowing steam into the thin film evaporator to contact the moving liquid film (counter current). The alkyl glycoside was treated at 140° C. and 80 mmHg. The alkyl glycoside product thus obtained was substantially undeteriorated in hue or odor.

Table 1 summarizes the processing conditions and results.

EXAMPLE 2

The alkyl glycoside reaction product obtained in Example 1-(a) was introduced into a Smith thin film evaporator (heat transfer area of 0.032 m$^2$) to provide a moving liquid film thereof while blowing N$_2$ into the thin film evaporator to contact the moving liquid film (counter current). The alkyl glycoside was treated at 140° C. and 50 mmHg. The alkyl glycoside product thus obtained was substantially undeteriorated in hue or odor.

Table 1 summarizes the processing conditions and results.

EXAMPLE 3

(a) The procedure of Example 1-(a) was repeated except that the decyl alcohol was replaced with dodecyl alcohol. Thus, an alkyl glycoside reaction product containing unreacted dodecyl alcohol was obtained. Next, the excess dodecyl alcohol was distilled at 160° C. and 5 mmHg to provide an alkyl glycoside reaction product containing 3.2 % by weight of the unreacted dodecyl alcohol.

(b) The alkyl glycoside reaction product thus prepared was introduced into a Smith thin film evaporator (heat transfer area of 0.032 m$^2$) to provide a moving liquid film thereof while blowing steam into the thin film evaporator to contact the moving liquid film (counter current). The alkyl glycoside was treated at 150° C. and 50 mmHg. The alkyl glycoside product thus obtained was substantially undeteriorated in hue or odor.

Table 1 summarizes the processing conditions and results. The samples were evaluated for unreacted alcohol content, hue and odor.

COMPARATIVE EXAMPLE 1

The alkyl glycoside reaction product obtained in Example 1-(a) was introduced into a Smith thin film evaporator (heat transfer area of 0.032 m$^2$) to provide a moving liquid film thereof, while blowing steam into the thin film evaporator to contact the moving liquid film (counter current). The alkyl glycoside was treated at 210° C. and 100 mmHg. As a result, the hue of the alkyl glycoside was noticeably deteriorated and the average degree of saccharide chain length of the product increased from 1.3 to 1.5. These results indicate a deterioration in the quality of the alkyl glycoside product.

Table 1 summarizes the processing conditions and results.

COMPARATIVE EXAMPLE 2

The procedure of Example 1 was repeated, except that no steam was blown into the thin film evaporator.

Table 1 summarizes the processing conditions and results.

COMPARATIVE EXAMPLE 3

The alkyl glycoside reaction product obtained in Example 1-(a) was introduced into a Smith thin film evaporator (heat transfer area of 0.032 m$^2$) and treated therein at 180° C. and 0.5 mmHg. No steam or inert gas was blown into the thin film evaporator.

Table 1 summarizes the processing conditions and results.

TABLE 1

| | Feed Rate (kg/hr) | Treating Temperature (°C.) | Pressure (mmHg) | Blowing Rate of Steam or Nitrogen | Content of unreacted alcohol | | Hue | | Odor* After treatment |
|---|---|---|---|---|---|---|---|---|---|
| | | | | | Initial (% by wt.) | After treatment (% by wt.) | Initial (Gardner) | After treatment (Gardner) | |
| Example 1 | 10 | 140 | 80 | Steam 13 kg/Hr | 2.8 | 0.038 | 3 | 4 | A |
| Example 2 | 0.125 | 140 | 50 | N$_2$ 234 l/Hr | 2.8 | 0.045 | 3 | 3 | A |
| Example 3 | 0.012 | 150 | 50 | Steam 0.15 kg/Hr | 3.2 | 0.063 | 3 | 4 | A |
| Comparative Example 1 | 0.120 | 210 | 100 | Steam 0.163 kg/Hr | 2.8 | 0.093 | 3 | 8 | A |
| Comparative Example 2 | 10 | 140 | 80 | 0 | 2.8 | 0.783 | 3 | 4 | C |
| Comparative | 0.115 | 180 | 0.5 | 0 | 2.8 | 0.55 | 3 | 6 | B |

TABLE 1-continued

| | Feed Rate (kg/hr) | Treating Temperature (°C.) | Pressure (mmHg) | Blowing Rate of Steam or Nitrogen | Content of unreacted alcohol Initial (% by wt.) | Content of unreacted alcohol After treatment (% by wt.) | Hue Initial (Gardner) | Hue After treatment (Gardner) | Odor* After treatment |
|---|---|---|---|---|---|---|---|---|---|
| Example 3 | | | | | | | | | |

Note *: Evaluation of odor:
A: Little irritating odor.
B: Irritating odor.
C: Intense irritating odor.

EXAMPLE 4

(a) 11400 g (72.2 mol) of decyl alcohol, 3240 g (18.0 mol) of anhydrous glucose and 96 g (0.5 mol) of p-toluenesulfonic acid monohydrate were heated and stirred in a 30 liter reaction vessel. After heating the mixture to 95° C., the pressure in the system was reduced to 40 mmHg so as to initiate dehydration, while blowing nitrogen gas into the reaction mixture at a rate of 0.3 Nm³/h to thereby efficiently remove the water thus formed. After 5 hours, it was confirmed that the reaction mixture has turned transparency, namely the glucose had been completely consumed. Then, the reaction vessel was vented to atmospheric pressure and the reaction mixture was cooled and neutralized with 20 g of NaOH. After filtering polysaccharides formed as by-products, the filtrate was distilled at 130° C. and 0.4 mmHg to separate 4270 g of an alkyl glycoside and 8460 g of the unreacted alcohol. A portion of the solid material was dissolved in water to obtain a 50 % aqueous solution of the alkyl glycoside. The hue of the product was Gardner 5.

(b) The thus prepared aqueous solution of the alkyl glycoside was introduced into a Smith thin film evaporator (manufactured by SHINKO PANTEC Co.; heat transfer area: 0.032 m²) to provide a moving liquid film thereof while blowing steam into the thin film evaporator to contact the moving liquid film (counter current). The alkyl glycoside was treated at 70° C. and 100 mmHg. As a result, no deterioration in the hue was observed, and the characteristic burnt smell originating from thermal decomposition was removed.

Table 2 summarizes the processing conditions and results.

EXAMPLE 5

(a) The aqueous solution of the alkyl glycoside obtained in Example 4-(a) was heated to 60° C. and the pH value thereof was adjusted to 9 by adding 10 g of a 3 % aqueous solution of NaOH. Then, 12 g of a 30 % aqueous solution of hydrogen peroxide was added thereto and the mixture was stirred at 60° C. for 30 minutes. The hue of the mixture thus treated was Gardner 3. Although the burnt smell originating from the thermal decomposition was removed, a newly generated rancidic and aldehyde-like smell was noticeable. (b) The alkyl glycoside aqueous solution was introduced into a Smith thin film evaporator (heat transfer area of 0.2 m²) to provide a moving liquid film thereof, while blowing steam into the thin film evaporator to contact the moving liquid film (counter current). the alkyl glycoside was treated at 80° C. and 200 mmHg. The alkyl glycoside product thus obtained showed no deterioration in hue and had an improved odor.

Table 2 summarizes the processing conditions and results.

COMPARATIVE EXAMPLE 4

The procedure of Example 5-(b) was repeated except that no steam was blown into the thin film evaporator.

Table 2 summarizes the processing conditions and results.

COMPARATIVE EXAMPLE 5

500 g of the alkyl glycoside aqueous solution obtained in Example 5-(a) was introduced into a 1 liter flask and treated therein at 70° C. and 300 mmHg for 5 hours with steam, while attending to foaming of the product. As a result, the odor of the product was improved, but the hue thereof was noticeably deteriorated.

Table 2 summarizes the processing conditions and results.

TABLE 2

| Treatment | Feed Rate | Treatment Temperature (°C.) | Pressure (mmHg) | Blowing Rate of Steam (kg/Hr) | Hue Initial (Gardner) | Hue After Treatment (Gardner) | Odor* Initial | Odor* After Treatment |
|---|---|---|---|---|---|---|---|---|
| Example 4 | 0.185 (kg/Hr) | 70 | 100 | 0.222 | 5 | 5 | B | A |
| Example 5 | 0.201 (kg/Hr) | 80 | 200 | 0.261 | 3 | 3 | C | A |
| Comparative Example 4 | 0.192 (kg/Hr) | 80 | 200 | 0 | 3 | 3 | C | C to B |
| Comparative Example 5 | 500 g (1 l flask) | 70 | 300 | 0.120 | 3 | 6 | C | B to A |

Note *: Evaluation of odor:
A: Little irritating odor.
B: Irritating odor.
C: Intense irritating odor.

According to the present invention, an alkyl glycoside or aqueous solution thereof is provided containing little unreacted alcohol and being excellent in hue and odor, advantageously and economically produced.

While the invention has been described in detail and with reference to specific examples thereof, it will be apparent to one skilled in the art that various changes and modifications can be made therein without departing from the spirit and scope thereof.

What is claimed is:

1. A process for the production of an alkyl glycoside or aqueous solution thereof, comprising the steps of (1) reacting a sugar with alcohol to obtain an alkyl glycoside reaction product containing unreacted alcohol, (2) establishing a moving liquid film of the alkyl glycoside reaction product, and (3) contacting the moving liquid film with steam or an inert gas at a temperature of from 50 to 200° C. to remove the unreacted alcohol.

2. A process as in claim 1, wherein the alkyl glycoside reaction product is obtained by reacting the sugar with a higher alcohol represented by formula (I):

$$R^1(OR^2)_xOH \quad (I)$$

wherein
- $R^1$ represents a straight-chain or branched alkyl, alkenyl or alkylphenyl group having from 6 to 22 carbon atoms;
- $R^2$ represents an alkylene group having from 2 to 4 carbon atom; and
- x indicates a mean value and is a number equal to 0 to 5.

3. A process as in claim 1, whrein the alkyl glycoside reaction product is obtained by:
first reacting the sugar with a lower alcohol selected from methanol, ethanol, propanol and butanol; and then
reacting the product thereof with a higher alcohol represented by formula (I):

$$R^1(OR^2)_xOH \quad (I)$$

wherein
- $R^1$ represents a straight-chain or branched alkyl, alkenyl or alkylphenyl group having from 6 to 22 carbon atoms;
- $R^2$ represents an alkylene group having from 2 to 4 carbon atoms; and
- x indicates a mean value and is a number equal to 0 to 5.

4. A process as in claim 1, wherein the unreacted alcohol content of the thus produced alkyl glycoside or aqueous solution thereof is reduced to an amount of 0.5 % by weight or less based on the alkyl glycoside.

5. A process as in claim 1, wherein the unreacted alcohol content of the thus produced alkyl glycoside or aqueous solution thereof is reduced to an amount of 0.2 % by weight or less based on the alkyl glycoside.

6. A process as in claim 1, wherein the concentration of the unreacted alcohol in the alkyl glycoside reaction product is from 3 to 10 % by weight.

7. A process as in claim 1, wherein the moving liquid film is contacted with steam or an inert gas at a temperature of from 120° to 170° C.

8. A process as in claim 1, wherein the moving liquid film is contacted with steam or an inert gas at a pressure of 300 mmHg or less.

9. A process as in claim 1, wherein the moving liquid film is contacted with steam or an inert gas at a pressure of 150 mmHg or less.

10. A process as in claim 1, wherein the moving liquid film has a thickness of about 10 mm or less.

* * * * *